United States Patent [19]

Preuss

[11] 4,448,725
[45] May 15, 1984

[54] Δ4-STEROID COMPOUNDS AND A PROCESS FOR THEIR PRODUCTION

[75] Inventor: Wolfgang Preuss, Monheim, Fed. Rep. of Germany

[73] Assignee: Henkel KGaA, Duesseldorf, Fed. Rep. of Germany

[21] Appl. No.: 407,790

[22] Filed: Aug. 13, 1982

Related U.S. Application Data

[63] Continuation-in-part of Ser. No. 262,965, May 12, 1981, abandoned.

[30] Foreign Application Priority Data

May 12, 1980 [AT] Austria ................................ 2535/80

[51] Int. Cl.³ .............................................. C07J 9/00
[52] U.S. Cl. ............................. 260/397.1; 260/397.3; 260/397.45
[58] Field of Search ...................................... 260/397.1

[56] References Cited

U.S. PATENT DOCUMENTS 2,752,369  6/1956  Holysz et al. .................. 260/397.45
3,539,687 11/1970  Kuhnen et al. ...................... 424/241
4,255,345  3/1981  Krbechek ........................ 260/397.1

Primary Examiner—Elbert L. Roberts

Attorney, Agent, or Firm—Ernest G. Szoke; Nelson Littell, Jr.

[57]                  ABSTRACT

New Δ4-steroid compounds optionally containing a further double bond in the 1-position and an 11-oxygen function and corresponding to general formula I below:

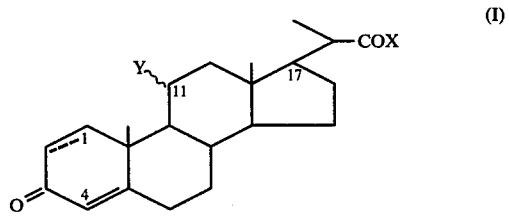

in which X represents halogen, particularly chlorine or bromine, or $NH_2$ and Y is a hydroxyl group, or together with the C-atom substituted by Y, represents a carbonyl group, are obtained from the associated steroid-20-carboxylic acids by reaction with a halogenating agent in substantially stoichiometric quantities at temperatures not exceeding 15° C., after which the steroid-20-carboxylic acid halide formed is, if desired, reacted with ammonia or with a compound which yields ammonia.

8 Claims, No Drawings

Δ4-STEROID COMPOUNDS AND A PROCESS FOR THEIR PRODUCTION

This application is a continuation-in-part of Ser. No. 262,965, filed May 12, 1981, now abandoned.

BACKGROUND OF THE INVENTION

European Patent Application No. 004 913 as laid open describes inter alia a process for the production of 17C-steroid-α-propionic acid compounds, particularly 3-oxopregna-4-ene-20-carboxylic acid (Δ4-BNC) and/or 3-oxopregna-1,4-dien-20-carboxylic acid (Δ1,4-BNC), by microbial side chain degradation on 17C-side chain steroid substrates. By using microorganism defect mutants grown and selected in a certain manner, which give steroid compounds containing the 17C-α-propionic acid residue, even in the absence of inhibitors which inhibit degradation of the steroid ring and/or growth, it is possible to obtain Δ4-BNC and, in particular, Δ1,4-BNC in commercial quantities. Another embodiment of this process is described in European Patent Application No. 0015 308.

These BNC compounds obtained by the side chain degradation of sterols (Δ4-BNC and Δ1,4-BNC) contain a functional group in only the 3-position of the ring system. However, all pharmacologically active corticosteroids contain additional oxygen functions. The 11,17- and 21-positions are particularly important in this respect. Normally some of these oxygen functions are chemically introduced, including, in particular, the 17- and 21-positions.

By contrast, oxidation of the 11-position in steroid compounds is preferably carried out microbially. Several microbial steroid oxidations in the 11-position are described in the specialist literature. In this connection, reference is made to the following publications and to the original articles cited therein:

(1) F. Drawert "Biosynthese von Hydroxy-Verbindungen (Biosynthesis of Hydroxy Compounds);"
(2) Houben-Weyl "Methoden der organischen Chemie" (1978) 6/ld, pp. 378–388;
(3) T. H. Stoudt, Adv. Appl. Microbial 2 (1960), pp. 190–195, and
(4) W. Charney and H. L. Herzog "Microbial Transformations of Steroids" Academic Press (1967), New York, page 29.

The microbial 11-hydroxylation of a variety of steroid compounds and the synthesis products obtained are described in these publications with numerous references to certain microorganism strains, particularly from the class of fungi.

The 11 β-hydroxyl or 11-oxo configuration is generally required for strong pharmacological activity. Steroids hydroxylated in the 11β-position are obtained either by using microorganism strains which introduce a hydroxyl group of the type in question stereoselectively or by using other microorganisms which hydroxylate in the 11β-position either predominantly or completely stereoselectively. In this case, the 11β-hydroxylated steroids are obtained by chemical oxidation to the 11-ketone in a first step, followed by reduction with a suitable reducing agent. The 11β-hydroxy compound can be formed stereoselectively. So far as the relevant literature on this subsequent chemical transformation is concerned, reference is made, for example, to L. F. Fieser, M. Fieser "Steroide (Steroids)," Verlag Chemie (Weinheim 1961), page 73 et seq. and to the original literature reference cited therein, J. Am. Chem. Soc. 77, 4436 (1955).

BNC-compounds having an oxygen function in the 11-position are described in DE-OS No. 28 39 033 which relates in particular to the production of 11α- and/or β-hydroxy Δ1,4-BNC and 11-keto-Δ1,4-BNC by microbial oxidation of the corresponding BNC-compounds with hydrogen in the 11-position.

OBJECTS OF THE INVENTION

The object of the present invention is to transform 11-oxidized steroid carboxylic acids containing a carboxyl group in the 20-position into functional derivatives of the type which may serve as suitable starting materials for a further chemical transformation.

Another object of the invention is in particular to provide new 20-steroid carboxylic acid derivatives having an oxygen function in the 11-position which are suitable for the stated purpose.

DESCRIPTION OF THE INVENTION

In a first embodiment, therefore, the present invention related to new Δ4-steroid derivatives optionally containing a further double bond in the 1-position and an 11-oxygen function and corresponding to general formula I:

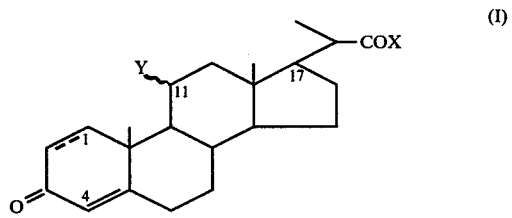

in which X is halogen or $NH_2$ and Y is a hydroxyl group or, together with the C-atom in the 11-position substituted by Y, represents a carbonyl group. The preferred halogens are bromine, but above all chlorine. The present invention also relates to processes for producing the compounds corresponding to general formula I which will be described in more detail hereinafter and to the new steroid derivatives corresponding to general formula I.

The new steroid-20-carboxylic acid derivatives according to the invention are derived from two basic types, namely, the steroid-20-carboxylic acids—each containing the oxygen function Y in the 11-position—corresponding to Δ4-BNC and to Δ1,4-BNC. The invention is described in detail in the following with reference to Δ1,4-BNC and its derivatives, but is by no means limited thereto, the corresponding Δ4-compounds also falling within the scope of the invention.

In a first special embodiment, the present invention relates to 11-hydroxy-pregna-1,4-dien-3-one-20-carboxylic acid derivatives corresponding to general formula II:

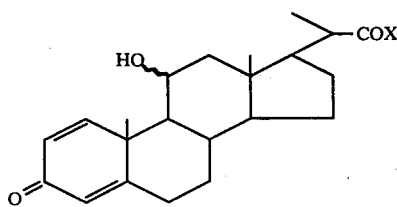

(II)

in which X is as defined above, i.e., represents in particular chlorine or bromine or NH$_2$. The hydroxyl group in the 11-position may be in the α- or β-form. Both embodiments fall within the scope of the invention. For the reasons explained above, namely, increased pharmacological activity, compounds of general formula II containing a β-hydroxy group are again particularly significant. The most important compounds of the type under discussion here are, therefore, 11β-hydroxy-pregna-1,4-dien-3-one-20-carboxylic acid chloride and the corresponding 20-carboxylic acid amide or the comparable compounds of Δ4-BNC.

If desired, 11α-hydroxy derivatives of the type in question may be transformed in known manner into corresponding 11β-hydroxy compounds, cf. the prior art literature cited at the beginning.

In another special embodiment, the invention relates to steroid derivatives of the type specified in which Y, together with the C-atom substituted by Y, represents a carbonyl group. The derivatives in question here are in particular pregna-1,4-dien-3,11-dione-20-carboxylic acid derivatives corresponding to general formula III:

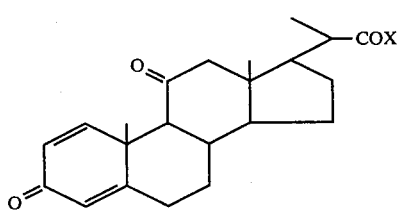

(III)

in which X represents halogen, particularly chlorine, or NH$_2$. Particularly important compounds are pregna-1,4-dien-3,11-dione-20-carboxylic acid chloride, the corresponding 20-carboxylic acid amide and the comparable derivatives of Δ4-BNC.

Halides and amides of the type under discussion here have never been described in the literature. They are particularly suitable for use as starting material for subsequent reactions for the further structural transformation of the side chain substituent in the 17-position of the steroid ring skeleton.

The production of the new compounds corresponding to general formula I and the characterization of certain important compounds by analytical data are described in detail in the following examples. However, the following observations apply generally to the production of the new compounds.

The conversion of carboxylic acids into acid halides, particularly acid chlorides, using halogenating agents, such as phosphorus halides, oxalyl halide or, in particular, thionyl halide, is a reaction which has long been known and generally used, even in the series of 20-carboxy pregnane derivatives.

However, if the reaction conditions described in the literature for the reaction of 3-acetoxy-bis-norcholenic acid with thionyl chloride (cf. for example, Fiat Final Report No. 966, page 24 et seq. and P. L. Julian, E. D. Meyer and H. C. Printy, J. Am. Chem. Soc. 70, 887 [1948]) are applied, for example, to Δ1,4-BNC and if the acid chloride thus obtained is subsequently esterified with methanol and the crude product analyzed, the gas chromatogram shows an additional peak while elemental analysis reveals a distinct, initially unexpected Cl-content. The same applies to an even greater extent where oxalyl chloride is used instead of thionyl chloride.

The reason for the occurrence of these undesirable impurities, which distinctly reduce the yield of required product and can give rise to purification problems in further reactions involving the acid chloride probably lies in chlorination, optionally followed by aromatization, of the A-ring in the steroid skeleton, as known, for example, for the reaction of androsta-1,4-dien-3,17-dione (ADD) with oxalyl chloride; cf. G. B. Moersch et al, J. Org. Chemistry, 29, 2495 (1964).

Surprisingly, the acid halides required in accordance with the invention are formed under such mild reaction conditions that there is no undesirable co-reaction of other reactive sites of the parent mono-unsaturated or poly-unsaturated BNC-structure. Thus, it has surprisingly been found that, for example, substantially quantitative acid chloride formation takes place when the following reaction conditions are applied: reaction temperatures below 15° C., preferably below 5° C. and, more particularly, in the range of from 0° to 5° C., stoichiometric quantities of the reactants or only a very slight excess of the halogenating agent which preferably amounts to no more than 20 mol percent and, more particularly, to no more than 10 mol percent and working in the presence of an inert diluent, if desired, in the presence of small quantities of a basic catalyst.

Suitable inert solvents are, for example, halogenated hydrocarbons or, with limitations, ethers. Suitable halogenated hydrocarbons are, for example, methylene chloride or chloroform. Suitable halogenating agents are phosphorus halides, particularly PCl$_3$ or PCl$_5$, and the corresponding bromides, but above all thionyl halide, particularly thionyl chloride. Catalytic quantities of a base, particularly pyridine or dimethyl formamide, accelerate the reaction, but are frequently unnecessary. In individual cases, it may be desirable to use a catalyst, as for example, in the production of the acid chloride of 1,4-11β-OH-BNC. Pyridine is preferably used as the catalyst.

Depending on the other process parameters and on the compounds to be reacted with one another, individual process parameters may even lie beyond the limits hitherto quoted. Thus, the process temperature, for example, may be in the range from about −20° C. to about 75° C., provided that, at the higher temperatures of this range, the formation of undesirable ring halogenation products is avoided by suitably controlling the process. The quantity in which the halogenating agent is used may also considerably exceed the stoichiometrically necessary quantity, again with the proviso that the other process conditions are suitably adapted. Thus, for example, quantities of up to five equivalents and preferably up to three equivalents of the halogenating agent may be used in special cases. The reaction is usually carried out at normal pressure. The halogenating agent is best added to a solution of the steroid compound to be reacted in the inert solvent. It has proved to be of advantage to use the halogenating agent in the purest possible form. Impurities normally present in the halogenating agent evidently promote undesirable secondary reactions. For example, it is advisable to purify the halogenating agent with an unsaturated compound, such as linseed oil or, more particularly, squalene. These unsaturated components react with the impurities in the halogenating agent and thus reduce the formation of undesirable secondary products to a minimum.

The new carboxylic acid amides according to the invention corresponding to general formula I, i.e., compounds in which X represents the $NH_2$-group, may be obtained from the acid halides. They are obtained by reacting the associated 20-carboxylic acid halide with ammonia or a compound which yields ammonia. This reaction is best carried out at temperatures in the range from about $-20°$ C. to about $80°$ C. and preferably at temperatures in the range from about $-5°$ C. to about $35°$ C. Ammonia or the compound which yields ammonia under the reaction conditions is used in at least substantially equimolar quantities. For example, the ammonia or ammonia-yielding compound may be used in quantities amounting to between 1.1 and 5 equivalents, based on the acid halide, and preferably in quantities amounting to between 1.2 and about 3 equivalents. If an ammonia-yielding compound rather than ammonia itself is used, ammonium hydroxide is particularly suitable for this purpose.

The reaction of the 20-carboxylic acid halide with ammonia or with the ammonia-yielding compound is again preferably carried out in an organic solvent, for example, in halogenated hydrocarbons as specified above. In this case too methylene chloride or chloroform is a particularly suitable inert solvent.

If ammonium hydroxide is used as the ammonia-yielding component, an aqueous phase accumulates in addition to the organic phase in the reaction mixture. The reaction product may be recovered by simple phase separation or even by separating off the amide precipitated in solid form. The organic phase separated off is best repeatedly washed with water, subsequently dried, for example, with calcium sulfate, and filtered. The organic solvent used as the inert diluent is separated off, after which the carboxamido compound may be further purified in known manner.

Any hydrohalic acid released during the reaction between the carboxylic acid halide and ammonia is either bound by an excess of ammonia or ammonium hydroxide or, alternatively, a basic compound may be used for binding the acid released.

The 11-oxo- compound may also be obtained by oxidation of the corresponding 11-hydroxy compounds. In this case, therefore, the target compounds may be directly obtained not only from 11-oxo starting materials but also from 11-hydroxy starting compounds.

Both the steroid-20-carboxylic acid halides described at the beginning, particularly the corresponding chlorides, and also the 20-carboxylic acid amides obtained therefrom are valuable starting products for further transformation of the substituent in the 17C-position.

In particular, the steroid-20-carboxylic acid halide is converted to the corresponding carboxylic acid azide, which in turn is transformed into the C-20-amine as described in my copending U.S. patent application Ser. No. 262,967, filed May 12, 1981, now abandoned in favor of continuation-in-part Ser. No. 407,791, filed Aug. 13, 1982.

The compounds of formula I where X represents a halide are reacted with a metal azide in an aqueous/organic two-phase reaction at a temperature of below about $25°$ C. and the resulting carboxylic acid azide is further processed by a reaction selected from the group consisting of:

(a) recovery of the azide and heating to give the C-20-isocyanate by the elimination of nitrogen and, optionally, the C-20-isocyanate thus obtained is converted into the C-20-carbamate or the C-20-amine, and (b) hydrolyzing the azide by heating in the presence of an aqueous acid with elimination of nitrogen into the C20-amine, and recovering said $\Delta 4$-C21-steroid compounds having the formula IV:

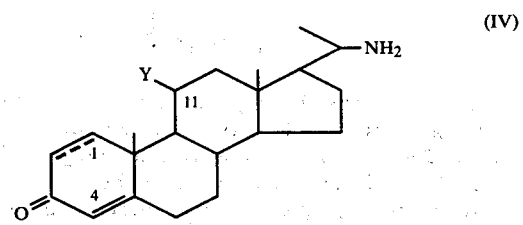

where Y has the above-assigned values.

These compounds of formula IV are useful for the production of steroid compounds having the acetyl side chain of progesterone in accordance with the following scheme:

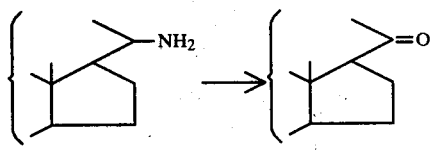

The method described in U.S. Pat. No. 4,252,732 for converting the 20-amino group to the 20-oxo group can be followed in all instances. The method described by patentee in Example 1 can also be applied to the compounds of formula IV which have an oxygenated function in the 11-position. For example, by following the process of Example 1 of the patent, 20-amino-pregna-1,4-dien-3,11-dione will give the known compound pregna-1,4-dien-3,11,20-trione, and 20-amino-11$\beta$-hydroxy-pregna-1,4-dien-3-one will give the known compound pregna-1,4-dien-11$\beta$-ol-3,20-dione. Both these 20-keto compounds are described in U.S. Pat. No. 2,128,238.

The conversion of the 20-amine to the 20-keto effected by the agency of 3,5-di-tert.-butyl-1-benzoquinone according to Example 1 of U.S. Pat. No. 4,252,732 can be applied to the above compounds of formula IV.

The above specifically mentioned keto compounds, as well as other keto compounds derived from the compounds of formula IV can be transformed, in analogy to the process of Hogg et al, J. Am. Chem. Soc., 77, 4438 (1955) into 17(20)-en-21-carboxylated steroids:

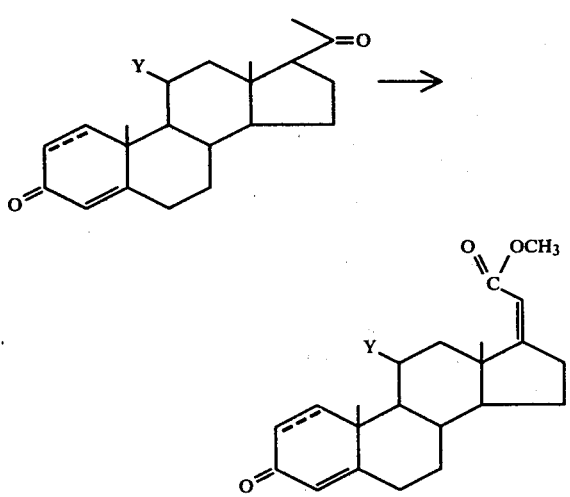

By the process above, pregna-1,4-dien-3,11,20-trione will give the methyl ester of 3,11-dioxo-pregna-1,4,17(20)-trien-21-carboxylic acid and pregna-1,4-dien-11β-ol-3,20-dione will give the methyl ester of 11β-hydroxy-3-oxo-pregna-1,4,17(20)-triene-21-carboxylic acid.

The further transformation of the 17(20)-unsaturated esters, via the respective 21-hydroxy-pregnane derivatives into corticoids, such as prednisone and prednisolone has likewise been described by Hogg et al, J. Am. Chem. Soc. 77, 4438 (1955) according to the following reaction scheme:

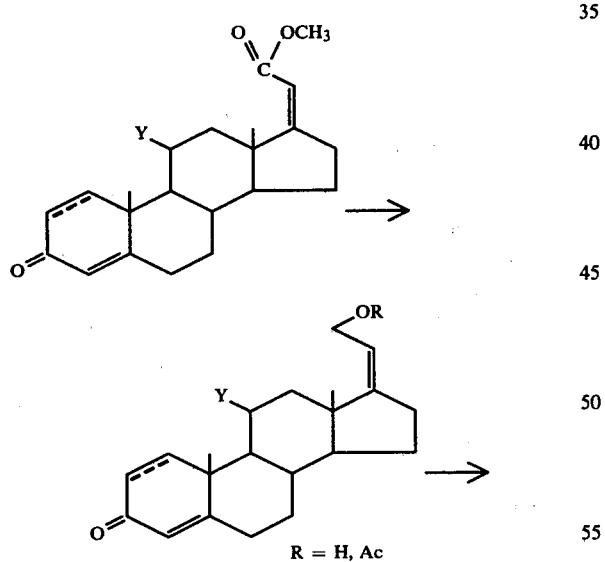

An improved reduction step for the above reaction is described in my commonly-assigned U.S. patent application Ser. No. 262,969, filed May 12, 1981, now U.S. Pat. No. 4,370,271.

Thus, according to the claimed method, access is opened up to intermediate products for pharmacologically effective corticoids such as prednisone and prednisolone.

EXAMPLE 1

Pregna-1,4-dien-3,11-dione-20-carbonyl chloride 0.12 ml (1.6 mMols) of thionyl chloride freshly distilled over squalene and a small drop of pyridine are added at 0° C. to 500 mg (1.4 mMols) of Δ1,4,11-oxo-BNC in 8 ml of dry $CH_2Cl_2$. After one hour, the solvent and excess thionyl chloride were removed in vacuo at 0° C. 5 ml of absolute methylene chloride are added to the residue, followed by reconcentration to dryness. The crude acid chloride is obtained in a yield of 495 mg.

To verify the yield, the crude acid chloride was dissolved in 10 ml of absolute methylene chloride and 2 ml of dry methanol and 0.5 ml of pyridine added to the resulting solution at 0° C. Quantitative TC-analysis after the ester formed had been transferred to a measuring cylinder revealed 470 mg (90%) of the methyl ester:

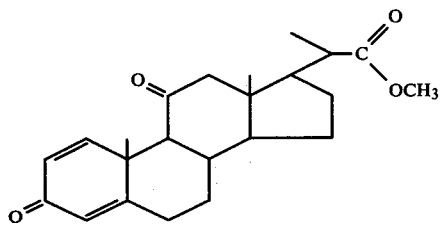

EXAMPLE 2

11β-hydroxy-pregna-1,4-dien-3-one-20-carbonyl chloride

This compound was prepared in the same way as in Example 1. To verify the yield, the reaction product was converted into the methyl ester. Yield: 88%

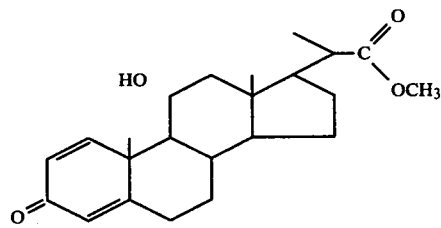

Results comparable with those obtained in Examples 1 and 2 are obtained where Δ4-BNC or mixtures of two of the components mentioned here are used.

EXAMPLE 3

Pregna-1,4-dien-3,11-dione-20-carboxamide

The acid chloride is prepared as in Example 1 from 1 gm of Δ1,4,11-oxo-BNC.

Dry $NH_3$ was introduced for five minutes into a solution thereof in 10 ml of dry methylene chloride, a white deposit precipitating. The reaction mixture was diluted with a little $CH_2Cl_2$ and then washed with dilute HCl, $NaHCO_3$-solution and then with water. After the $CH_2Cl_2$-phase had been dried over $Na_2SO_4$, it was concentrated to dryness and the residue stirred with ether.

Filtration left 880 mg of a white, crystalline residue which according to TC (silica gel; $CH_2Cl_2$/ethyl acetate/$CH_3OH$ 5:4:1 + 2% of triethylamine) contained only very few impurities.

Melting Point (from n-butanol): 220° to 225° C. (decomp.) $C_{22}H_{29}N_3$: Observed: C 74.08%, H 8.04%, N 3.78%, Calculated: 74.33%, 8.22%, 3.94%.

EXAMPLE 4

11β-hydroxy-pregna-1,4-dien-3-one-20-carboxamide 1 gm of Δ1,4,11-β-OH-BNC was converted into the chloride in the same way as described in Example 2.

After the $NH_3$ had been introduced, the reaction mixture was diluted with $CH_2Cl_2$ and cold 2 N HCl added thereto, the amide being partly precipitated in the form of a yellow-colored, greasy solid. This solid was separated off and dissolved in hot n-butanol. The amide crystallized out in the form of white crystals after prolonged standing.

A total of approximately 820 mg of the amide was obtained (pure fraction and quantities obtained from the solutions by concentration).

Melting point (from n-butanol): 260° C. (decomp.) $C_{22}H_{31}NO_3$: Observed: C 74.13%, H 8.89%, N 3.79%; Calculated: 73.91%, 8.74%, 3.92%.

I claim:

1. Δ4-Steroid compounds optionally containing further double bonds in the 1-position and an 11-oxygen function and corresponding to formula I:

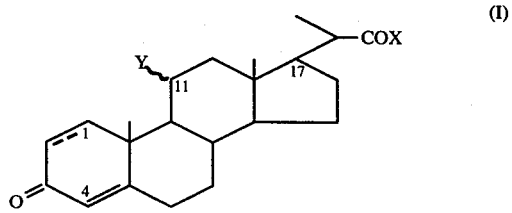

in which X represents a member selected from the group consisting of halogen and $NH_2$ and Y represents a member selected from the group consisting of hydroxy and, together with the C-atom substituted by Y, a carbonyl group.

2. The Δ4-steroid compounds of claim 1 wherein a double bond is present in the 1-position.

3. The Δ1,4-steroid compounds of claim 2 wherein Y is 11β-hydroxy.

4. The Δ1,4,11β-hydroxy steroid compounds of claim 3 wherein X is Cl.

5. The Δ1,4,11β-hydroxy steroid compounds of claim 3 wherein X is $NH_2$.

6. The Δ1,4-steroid compounds of claim 2 wherein Y is a keto group.

7. The Δ1,4-keto steroid compounds of claim 6 wherein X is Cl.

8. The Δ1,4-keto steroid compounds of claim 6 wherein X is $NH_2$.

* * * * *